(12) United States Patent
Beasley et al.

(10) Patent No.: US 10,384,035 B2
(45) Date of Patent: Aug. 20, 2019

(54) BALLOON CATHETER WITH ENHANCED LOCATABILITY

(71) Applicant: CLEARSTREAM TECHNOLOGIES LIMITED, Enniscorthy, County Wexford (IE)

(72) Inventors: Jim C. Beasley, Phoenix, AZ (US); Stephanie Klocke, Chandler, AZ (US); Abtihal Raji-Kubba, Phoenix, AZ (US); Rob Righi, Chandler, AZ (US)

(73) Assignee: CLEARSTREAM TECHNOLOGIES LIMITED, Enniscorthy (IE)

( * ) Notice: Subject to any disclaimer, the term of this patent is extended or adjusted under 35 U.S.C. 154(b) by 0 days.

(21) Appl. No.: 15/441,895

(22) Filed: Feb. 24, 2017

(65) Prior Publication Data

US 2017/0173302 A1 Jun. 22, 2017

Related U.S. Application Data

(62) Division of application No. 14/403,886, filed as application No. PCT/US2013/051863 on Jul. 24, 2013.

(60) Provisional application No. 61/788,938, filed on Mar. 15, 2013, provisional application No. 61/675,168, filed on Jul. 24, 2012.

(51) Int. Cl.
| | | |
|---|---|---|
| *A61M 25/00* | (2006.01) | |
| *A61M 25/01* | (2006.01) | |
| *A61M 25/10* | (2013.01) | |
| *A61B 90/00* | (2016.01) | |
| *A61M 25/09* | (2006.01) | |

(52) U.S. Cl.
CPC ...... *A61M 25/0108* (2013.01); *A61M 25/104* (2013.01); *A61B 90/39* (2016.02); *A61B 2090/3966* (2016.02); *A61M 25/09* (2013.01); *A61M 2025/1047* (2013.01); *A61M 2025/1068* (2013.01); *A61M 2025/1079* (2013.01)

(58) Field of Classification Search
CPC ........ A61M 2025/1079; A61M 25/104; A61M 25/0108; A61M 25/10; A61M 25/1002; A61M 2025/0008; A61M 2025/1068
See application file for complete search history.

(56) References Cited

U.S. PATENT DOCUMENTS

| | | | | |
|---|---|---|---|---|
| 4,793,359 A | * | 12/1988 | Sharrow | A61B 18/245 600/435 |
| 4,917,666 A | * | 4/1990 | Solar | A61M 25/1006 604/913 |
| 4,986,830 A | * | 1/1991 | Owens | A61M 29/02 604/913 |
| 5,135,486 A | * | 8/1992 | Eberle | A61M 25/104 604/103.1 |

(Continued)

*Primary Examiner* — William R Carpenter
(74) *Attorney, Agent, or Firm* — King & Schickli, PLLC

(57) ABSTRACT

A balloon catheter for insertion in a vessel includes a catheter shaft and an inflatable balloon attached to the catheter shaft. Markings along a longitudinal axis of the catheter are provided in an interior of the balloon, such as for measuring a distance within the vessel. A first distance separating a first marking from a second adjacent marking may be different from a second distance separating the second marking from the third adjacent marking. The markings may also be used for ensuring the proper positioning of the balloon and, in particular, the working surface thereof, relative to a treatment area.

20 Claims, 17 Drawing Sheets

(56) References Cited

U.S. PATENT DOCUMENTS

| | | | | |
|---|---|---|---|---|
| 5,547,472 | A * | 8/1996 | Onishi | A61M 25/104 |
| | | | | 604/103.01 |
| 7,322,958 | B2 * | 1/2008 | Wholey | A61B 17/22032 |
| | | | | 604/102.01 |
| 2005/0064224 | A1 * | 3/2005 | Bavaro | A61B 5/1076 |
| | | | | 428/615 |
| 2009/0254063 | A1 * | 10/2009 | Oepen | A61M 25/1006 |
| | | | | 604/509 |
| 2009/0270801 | A1 * | 10/2009 | Shimada | A61M 25/0023 |
| | | | | 604/96.01 |

* cited by examiner

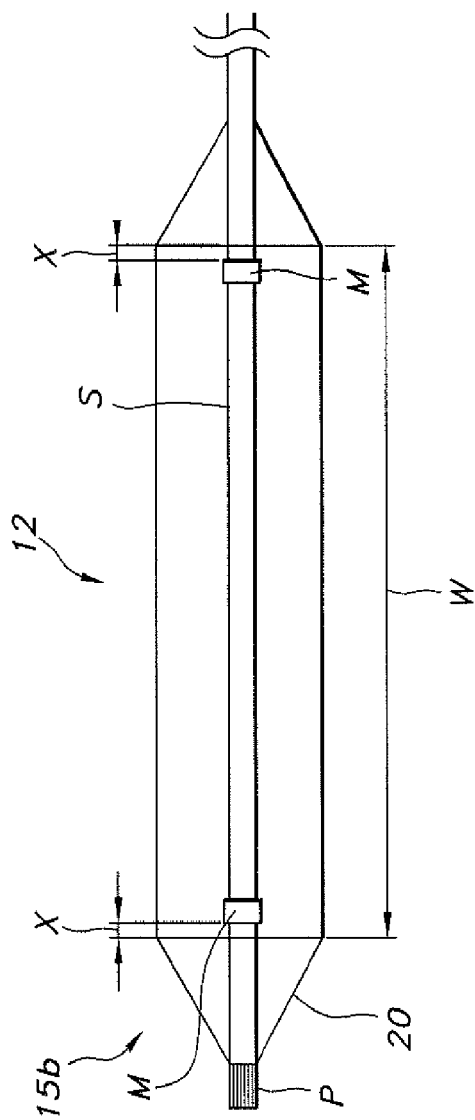

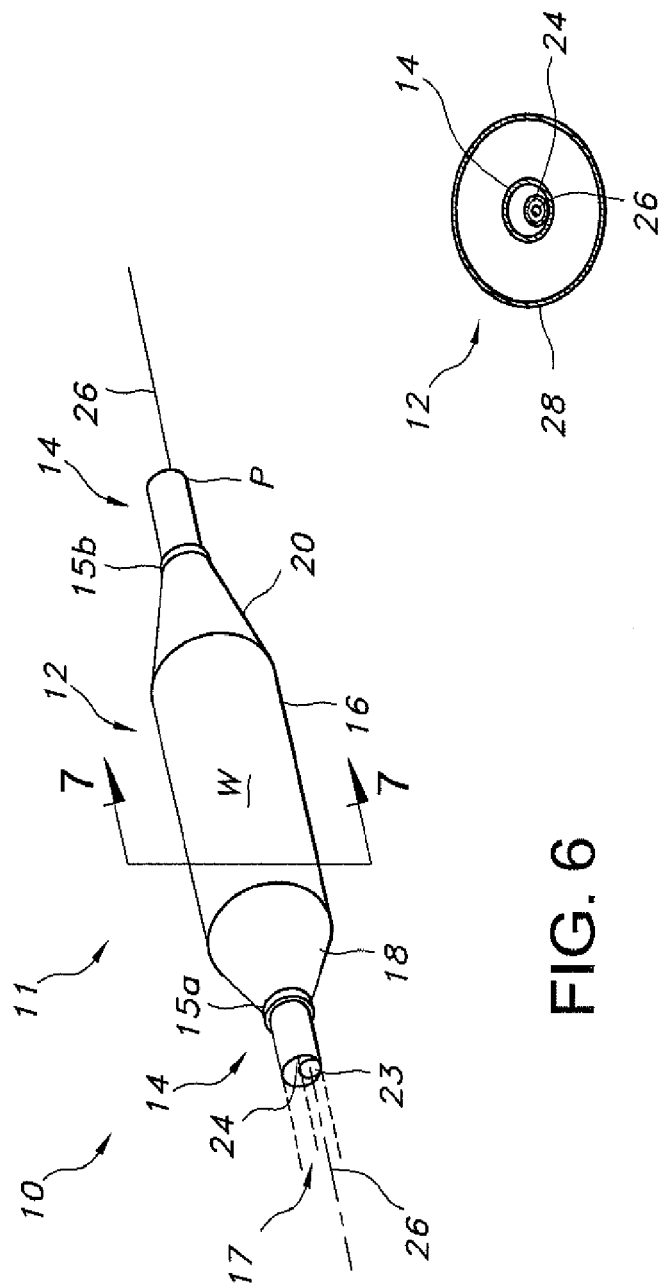

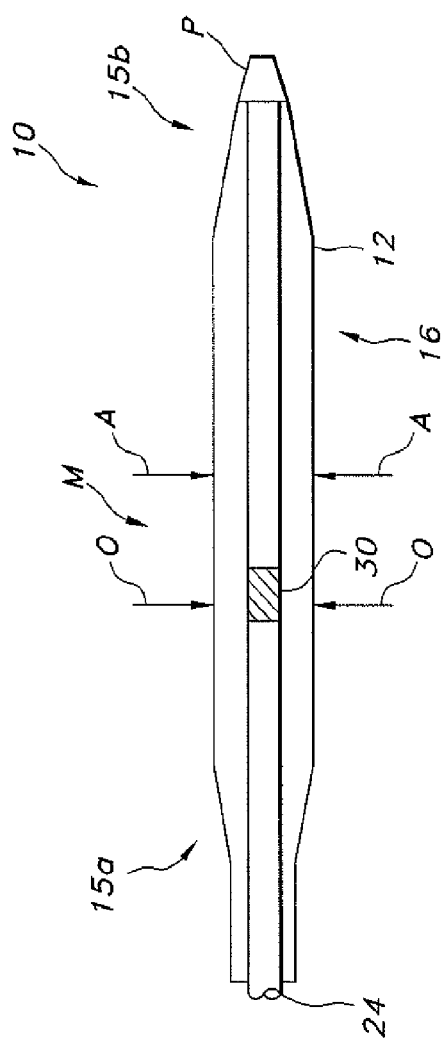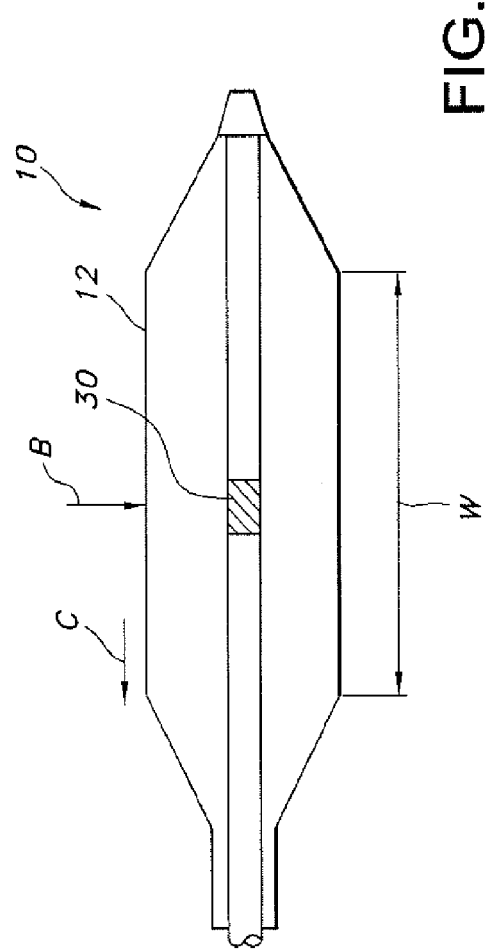

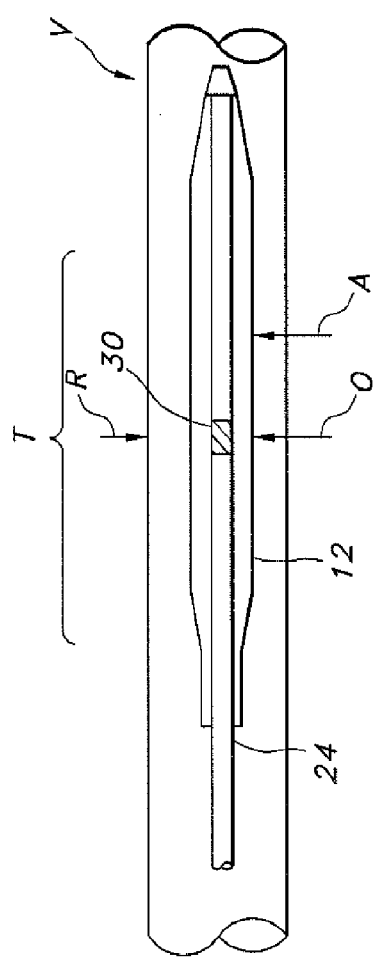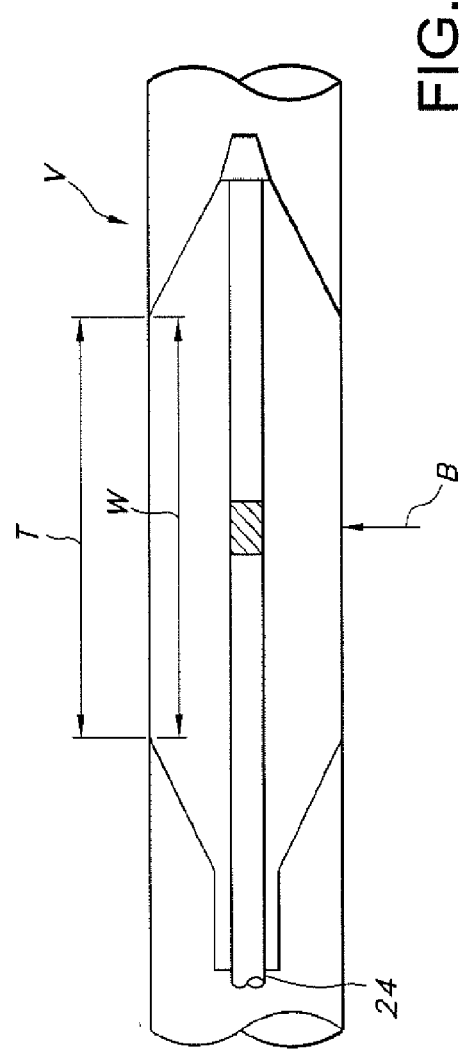

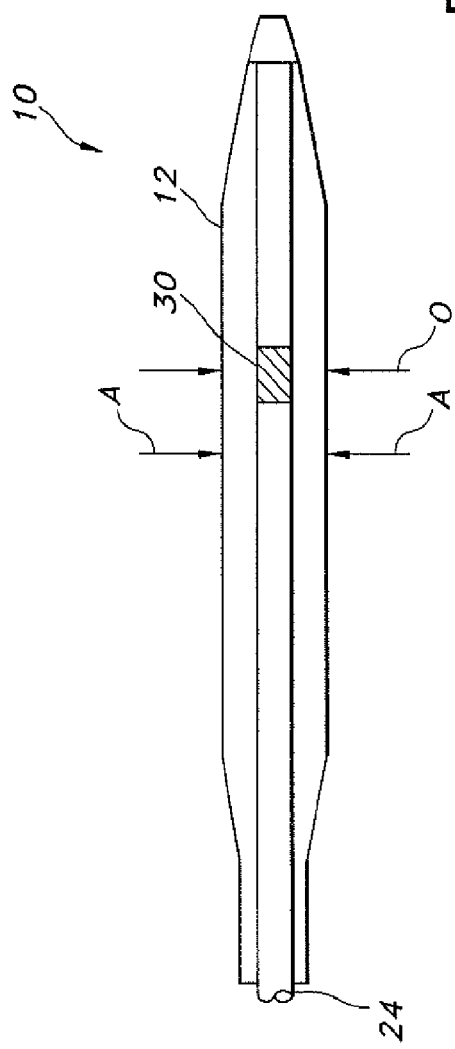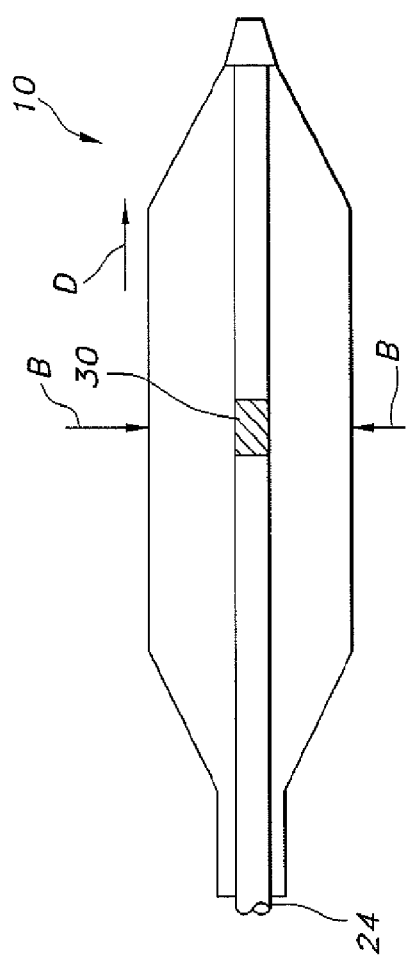

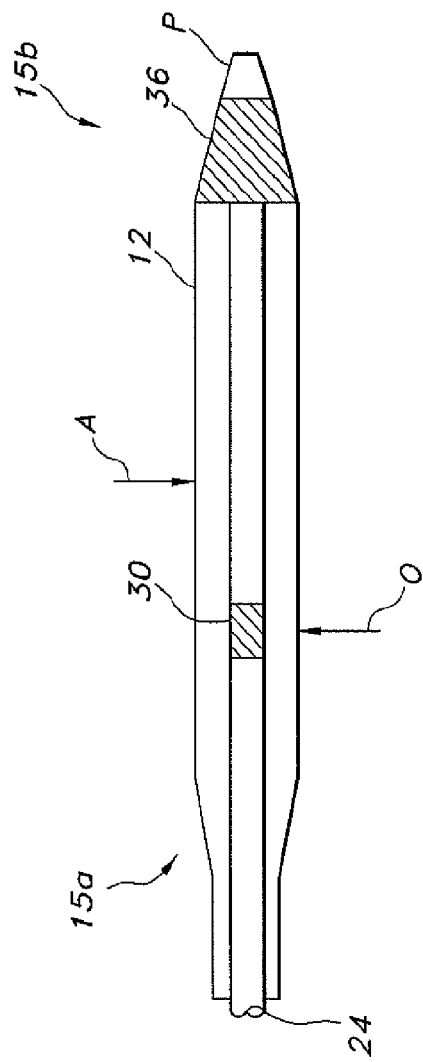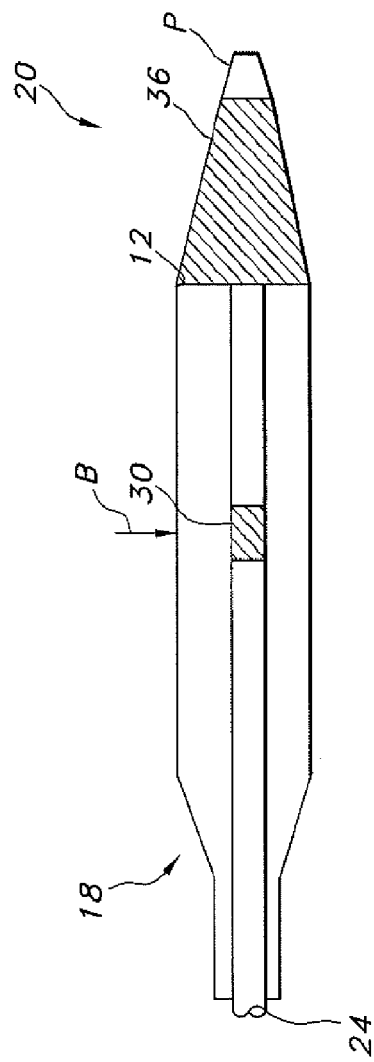

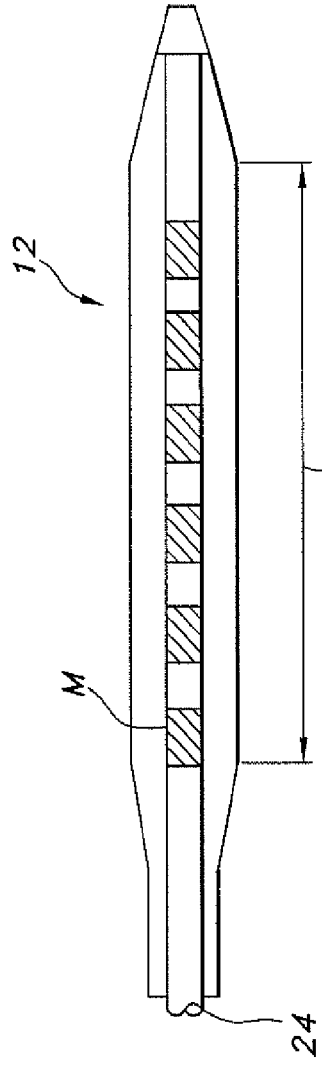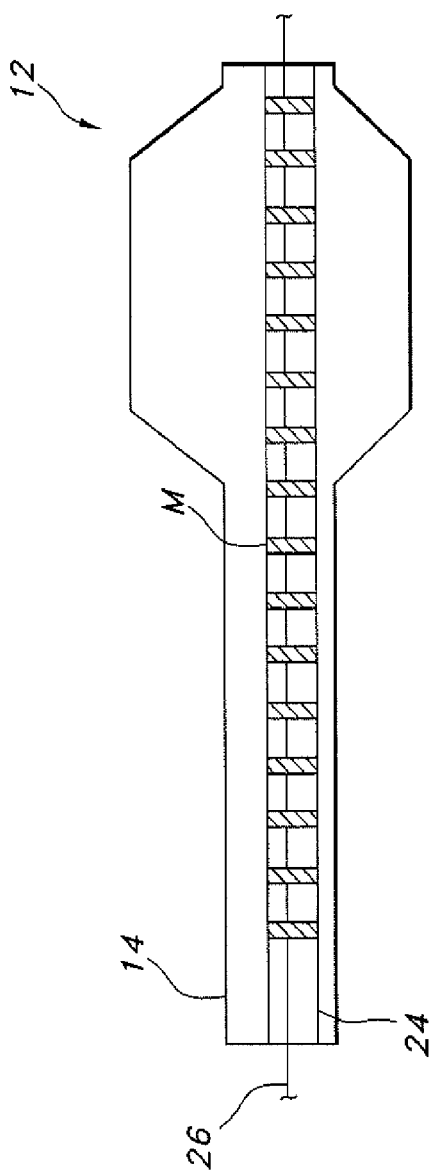

BALLOON CATHETER WITH ENHANCED LOCATABILITY

This application is a divisional of U.S. patent application Ser. No. 14/403,886, filed Nov. 25, 2014, which is a National Stage Patent Application of International Patent Application Ser. No. PCT/US2013/051863, filed Jul. 24, 2013, which claims the benefit of U.S. Provisional Patent Application Ser. Nos. 61/675,168, filed Jul. 24, 2012, and 61/788,938, filed Mar. 15, 2013, the disclosures of which applications are incorporated herein by reference.

TECHNICAL FIELD

This disclosure relates generally to balloon catheters for performing medical procedures, such as angioplasty and, more particularly, to a catheter having a predetermined portion, such as a working surface, that may be precisely located or identified during use.

BACKGROUND OF THE INVENTION

Catheters including balloons are routinely used to resolve or address flow restrictions or perhaps even complete blockages in tubular areas of the body, such as arteries or veins. In many clinical situations, the restrictions are caused by hard solids, such as calcified plaque, and may sometimes involve the use of high pressures to compact such blockages. Commercially available balloons employ complex technology to achieve high pressure requirements without sacrificing the profile of the balloon. Besides high pressure requirements, the balloons should also be resistant to puncture, easy to track and push, and present a low profile, especially when used for angioplasty.

In clinical practice, an angioplasty balloon 12 may be expanded from a deflated, folded state (FIG. 1) to an inflated, expanded state (FIG. 2) within a vessel at a treatment area T, such as a portion of the circumferential inner wall of a blood vessel V. The inflation may be completed using an X-ray contrast agent or media CM filling the balloon 12 to a height DX to provide better visibility under X-ray energy XR or other form of radiography during the interventional procedure, as illustrated in FIGS. 3 and 4. Typically, a 70/30 percent mixture of contrast agent and saline is used to inflate the balloon during an angioplasty procedure.

In general, a desirable goal is to reduce inflation and deflation times required for balloons without sacrificing the profile of the balloons, especially for large volume balloons (which can require up to two minutes of inflation/deflation times with the contrast agent). Because of its relatively high viscosity, it would also be desirable to eliminate, or at least reduce the amount of, the contrast agent used in inflation/deflation of the balloons. The use of contrast agent prolongs the inflation/deflation times and also poses the risk of iodine exposure to patients sensitive to iodine. In this regard, a non-radiopaque substance could be used in lieu of the contrast agent, such as for example saline or carbon dioxide, but such substances are invisible during X-ray imaging, and thus do not help with locating the balloon 12 in the desired manner.

Furthermore, the clinician performing the angioplasty procedure should be able to locate the position of the uninflated balloon with accuracy, so that the balloon will be properly positioned once inflated. This is conventionally accomplished by attaching marker bands on the catheter shaft corresponding to the ends of the balloon working surface. This "working surface" is the surface along the portion of the balloon that is used to achieve the desired treatment effect, such as contacting the calcified plaque (which surface in the case of a balloon having conical or tapering sections at the proximal and distal ends is typically co-extensive with a generally cylindrical barrel section).

Misalignment of the marker bands during placement along the shaft sometimes results in their failure to correspond precisely to the extent of the working surface, as is shown in FIG. 5 (note misalignment amount X between each interior marker band serving as marking M carried by shaft S and working surface W of balloon 12, which also typically includes a radiopaque tip P at the distal end). Even upon exercising great care to position the markings properly on the underlying shaft in alignment with anticipated boundaries of the working surface when the balloon is inflated, a tendency for mismatch remains due to several possible factors. One such factor may be the tolerance stack-ups arising as a consequence of the affixation of the balloon to the distal end of the catheter shaft. The balloon also has a tendency to grow in the longitudinal direction when inflated, especially with large and particularly long balloons. Another factor is the tendency of the portion of the catheter shaft within the balloon to bend or flex during inflation. This may lead to mis-alignment between markings M fixed to the shaft S and the working surface W.

Whatever the cause, the resulting misalignment may prevent the clinician from accurately identifying the location of the working surface of the balloon during an interventional procedure. This may lead to a geographic misplacement, or "miss," of the intended contact between the treatment area and the working surface of the balloon. It is especially desirable to avoid such an outcome when the balloon is designed to deliver a payload (such as a drug, stent, or both) or a working element (such as a cutter, focused force wire, or the like) to a specified location within the vasculature, since a miss may prolong the procedure (such as, for example, by requiring redeployment of the balloon or the use of another balloon catheter in the case of a drug coated balloon).

In order to assess the length of a lesion from a location external to the body, a clinician may also use an external ruler, which in one form is called a "LeMaitre" tape. While the use of such a ruler or tape may allow for a more precise assessment of the lesion length and an area treated by a pre-dilatation step, it is not without limitations. For one, a displacement or difference in the apparent position of the lesion margins results when viewed along two different lines of sight. This "parallax" can lead to an inaccurate measurement and, at a minimum, contribute to the geographic misalignment of the working surface relative to the lesion. The use of such an external ruler may also lead to inferior measurements when the vasculature at issue is particularly tortuous.

Accordingly, there is a need for a balloon for which the working surface may be identified during an interventional procedure with enhanced precision. One solution would take into account the possible mismatch between fixed locations on the catheter shaft and the balloon to define the working surface. Another would provide for a manner in which to position a balloon catheter into the vasculature at a treatment area with enhanced accuracy. Overall, procedural efficiency would be enhanced without remarkably increasing cost or complexity, and in a manner that can be applied to many existing catheter technologies without extensive modification.

SUMMARY

An object of the disclosure is to provide a balloon for which the working surface may be located during an interventional procedure with enhanced precision. A further object is to facilitate measuring a location within the vasculature, such as for providing a treatment during a subsequent intervention.

In accordance with one aspect of the disclosure, a balloon catheter for insertion in a vessel for treating a treatment area includes at least three radiopaque markings or markers spaced along a longitudinal axis of the catheter within the interior of the balloon. A first distance separating a first radiopaque marker or marking from a second adjacent radiopaque marking or marker is different from a second distance separating the second radiopaque marking or marker from a third adjacent radiopaque marking.

In one embodiment, a catheter shaft further includes an inner tubular member forming a guidewire lumen, and which the tubular member includes the at least three radiopaque markings or markers. The catheter shaft may include an outer wall having at least one of the first or second radiopaque markings or markers. The at least three markings or markers may be spaced from a distal tip of the catheter.

The first distance may be smaller than the second distance. The first radiopaque marking or marker may be distal to the second radiopaque marking, which may be distal to the third radiopaque marking or marker along the longitudinal axis. The radiopaque markings or markers may be arranged in a pattern comprising a plurality of adjacent pairs, with adjacent pairs being alternatingly separated by the first and second distances. A pattern of radiopaque markings or markers may comprise adjacent radiopaque markings or markers spaced at progressively larger distances from one another from a distal point on the catheter to a proximal point on the catheter.

In these or other embodiments, the balloon includes an uninflated midpoint location and an inflated midpoint location. The catheter shaft includes at least one first radiopaque marking or marker positioned at an offset location relative to the uninflated midpoint location. On inflation of the balloon, the at least one radiopaque marking or marker substantially aligns with the inflated midpoint location.

The balloon catheter may further include a second radiopaque marking or marker corresponding to at least one end of the working surface of the balloon. The second radiopaque marking or marker may be provided on the balloon, or may be provided along an end section of the balloon adjacent to one end of the working surface. A third radiopaque marking or marker may also be provided at a location corresponding to another end of the working surface.

The offset location may be spaced from the uninflated midpoint location in a proximal or distal direction. As one example, the offset location may be spaced from the uninflated midpoint location a distance approximately 1-15% of a length between a distal end and a proximal end of the balloon in an inflated condition. However, the amount may vary depending on the circumstances.

The balloon catheter may further include at least one radiopaque marking or marker external to the interior of the balloon. The external radiopaque marking or marker may be located on the shaft. An outer, tubular shaft may form an inflation lumen for supplying an inflation fluid to the balloon, and the external radiopaque marking or marker may be located on the outer tubular shaft. A plurality of radiopaque markings or markers may be external to the interior of the balloon, and may be regularly or irregularly spaced.

Another aspect of the disclosure relates to a balloon catheter for insertion in a vessel for treating a treatment area, comprising a catheter shaft and an inflatable balloon attached to the catheter shaft. At least three radiopaque markings or markers extend along a longitudinal axis of the catheter. A first amount of non-radiopaque material separating a first radiopaque marking or marker from a second radiopaque marking or marker is different from (e.g., having a length greater than or less than) a second amount of non-radiopaque material separating the second radiopaque marking or marker from a third radiopaque marking.

In another aspect, the disclosure pertains to a balloon catheter including an elongated, tubular shaft. An inflatable balloon supported by the shaft includes an uninflated midpoint location and an inflated midpoint location. The shaft further includes at least one first radiopaque marking or marker positioned at an offset location relative to the uninflated midpoint location. On inflation of the balloon, the at least one radiopaque marking or marker substantially aligns with the inflated midpoint location.

In one embodiment, a second radiopaque marking or marker corresponds to at least one end of the working surface of the balloon. The second radiopaque marking or marker may be provided on the balloon, such as along a narrowed end section of the balloon adjacent one end of the working surface. Alternatively, the second radiopaque marking or marker may be provided on the shaft at a location corresponding to a first end of the working surface. A third radiopaque marking or marker may be provided on the shaft at a location corresponding to a second end of the working surface.

A further aspect of the disclosure relates to a balloon catheter having an elongated, tubular shaft and an inflatable balloon supported by the shaft. The balloon includes a working surface having a midpoint in an inflated condition. At least one first radiopaque marking or marker corresponds to the location of at least one end of the working surface in the inflated condition. At least one second radiopaque marking or marker corresponds to the location of the working surface midpoint.

The first radiopaque marking or marker may be located on the shaft. Further, a third radiopaque marking or marker corresponding to a second end of the working surface may also be provided. The third radiopaque marking or marker may be located on the shaft, and first radiopaque marking or marker on the balloon.

Yet another aspect of the disclosure pertains to a balloon catheter, comprising an elongated, tubular shaft and an inflatable balloon supported by the shaft. The balloon includes a working surface. First and second radiopaque markings or markers corresponding to the location of the ends of the working surface, respectively, and a third radiopaque marking or marker is positioned between the first and second radiopaque markings or markers.

The third radiopaque marking or marker may be closer to one of the first or second markings or markers in the longitudinal direction. One or both of the first and second radiopaque markings or markers may be provided on the shaft. The third radiopaque marking or marker may also be provided on the shaft or on the balloon.

The first radiopaque marking or marker may be closer to a proximal end of the balloon, and the third radiopaque marking or marker may be closer to the first marking or marker than the second marking. The second radiopaque marking or marker may be closer to a distal end of the balloon, and the third radiopaque marking or marker may be closer to the second marking or marker than the first marking.

In any of the disclosed embodiments, the balloon may be non-compliant, or may be compliant or semi-compliant. The balloon may further include a treatment, such as for example, a drug, stent, stent graft, or combinations of the foregoing. The balloon catheters of any of the foregoing embodiments may further include a guidewire for guiding the balloon within the vasculature. The markings or markers in any embodiment may comprise bands formed at least partially of a radiopaque material.

Any of the foregoing balloon catheters may be used in combination with another balloon catheter including a working surface corresponding in length to the spacing of at least two of the radiopaque markings or markers. The other balloon catheter may include a treatment corresponding in length to the spacing of at least two of the radiopaque markings or markers.

A further aspect of the disclosure relates to a balloon catheter comprising an elongated, tubular shaft, and an inflatable balloon supported by the shaft and having an interior. A plurality of first radiopaque markings or markers are provided proximal of the balloon. A plurality of second radiopaque markings or markers are provided within the interior of the balloon.

The tubular shaft may comprise an inner tubular shaft, and the first radiopaque markings or markers are provided on an outer tubular shaft coaxial with the inner tubular shaft. The first and second radiopaque markings or markers may be spaced equidistantly or non-equisitantly. The plurality of second radiopaque markings or markers may comprise at least three markings or markers.

The disclosure may also be considered to relate to the use of the balloon catheter or catheters of any of the foregoing claims in performing an angioplasty.

This disclosure also relates to methods of using a catheter to treat a treatment area. The catheter may include an inflatable balloon carried by a shaft including at least one radiopaque marking or marker offset from a midpoint location of the balloon in an uninflated condition. The method may comprise the step of aligning the offset radiopaque marking or marker (which may be on the shaft of the uninflated balloon) with a central region of the treatment area. The method may further include the step of inflating the balloon such that a working surface of the balloon when inflated corresponds to the treatment area.

A further aspect of the disclosure pertains to a method of measuring a distance within a vessel of a subject in combination with the use of a guidewire. The method comprises providing a catheter including a balloon and at least three radiopaque markings or markers within the balloon. The method further comprises determining a distance within the vessel using the markings or markers. The determining step may comprise measuring a length of a lesion within the vessel, and may be completed prior to the step of introducing a catheter including a treatment into the vessel.

This disclosure also describes a method of applying a therapeutic agent to a treatment area within a vessel of a subject. The method comprises the steps of: providing a measuring catheter including a plurality of radiopaque markings or markers; measuring a length of the treatment area using the measuring catheter; and providing a treatment balloon based on or corresponding to the measured length. The measuring catheter may comprise a balloon, and the method may further comprise inflating the balloon at the treatment site. The measuring step may be conducted prior to inflation of the balloon on the measuring catheter. The measuring step may be conducted subsequent to inflation of the balloon on the measuring catheter. The method may further comprise the step of positioning the treatment balloon at the treatment site to deliver a therapeutic agent to the treatment area. The method may further include the step of providing the treatment catheter with a balloon including a plurality of radiopaque markings or markers matching the markings or markers of the measuring catheter. The treatment catheter may include a balloon that is longer than the measuring balloon.

The present disclosure provides a balloon catheter comprising an elongated tubular shaft including a guidewire tubular member, an inflatable balloon supported by the shaft and having an interior, and a plurality of radiopaque markers along the guidewire tubular member both within the balloon and along the catheter outside of the balloon.

The catheters of any of the foregoing embodiments may be in combination with a guidewire, including during use.

BRIEF DESCRIPTION OF THE DRAWINGS

FIGS. 5-9 illustrate various embodiments of balloon catheters.

FIG. 10 is a partially cutaway, schematic side view showing an offset marking or marker on a balloon catheter according to one embodiment of the disclosure.

FIG. 11 is a side view of the catheter of FIG. 10 with the marking or marker in an aligned condition.

FIGS. 12 and 13 are partially cutaway, schematic side views illustrating use of the balloon catheter of FIG. 10.

FIGS. 14 and 15 are additional views of another embodiment of a balloon catheter according to the disclosure.

FIGS. 18 and 19 are additional views of still another embodiment of a balloon catheter according to the disclosure.

FIG. 20 is a partially cutaway, schematic side view showing a marking or marker pattern on a balloon catheter according to one embodiment of the disclosure.

FIG. 21 is a partially cutaway, schematic side view showing another version of a marking or marker pattern on a balloon catheter according to one embodiment of the disclosure

MODE FOR CARRYING OUT THE INVENTION

The description provided below and in regard to the figures applies to all embodiments unless noted otherwise, and features common to each embodiment are similarly shown and numbered.

Figure 1:
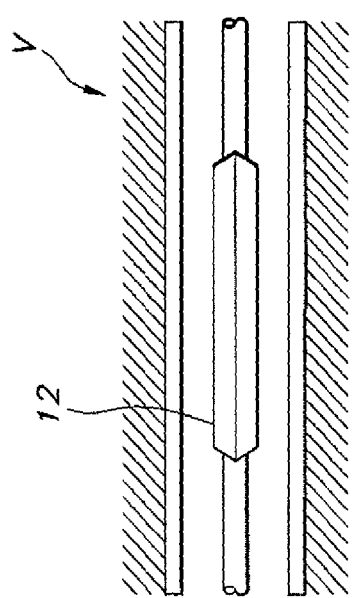
FIG. 1 illustrates schematically a balloon catheter in a vessel.
Figure 2:
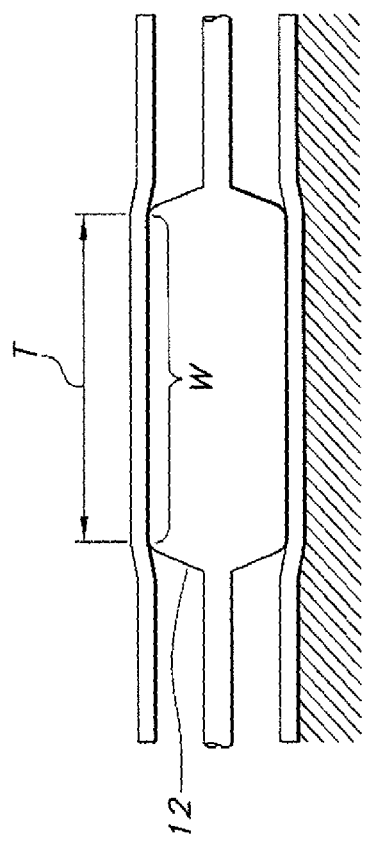
FIG. 2 illustrates the expanded balloon in the vessel.
Figure 3:
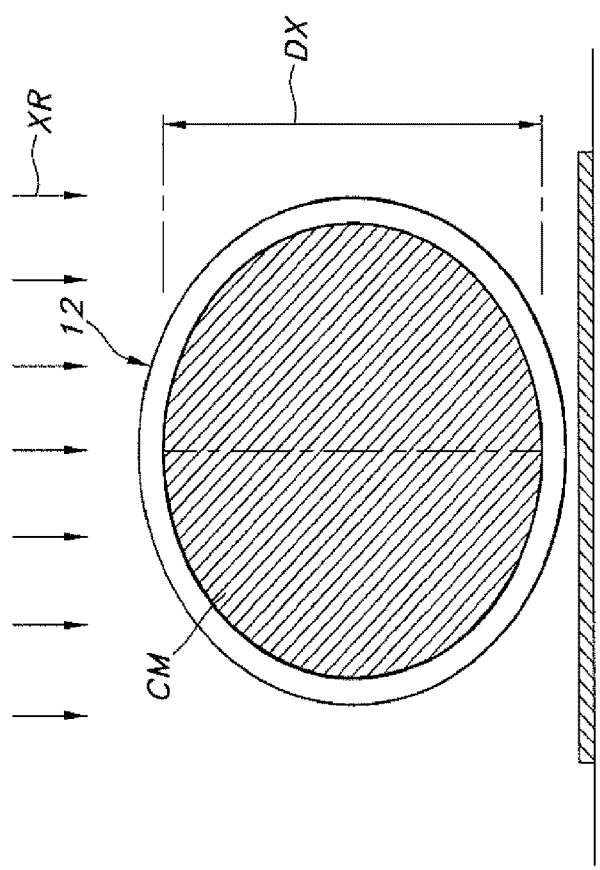
FIGS. 3 and 4 illustrate schematically the use of fluorescence to detect the balloon including a radiopaque contrast media.
Figure 4:
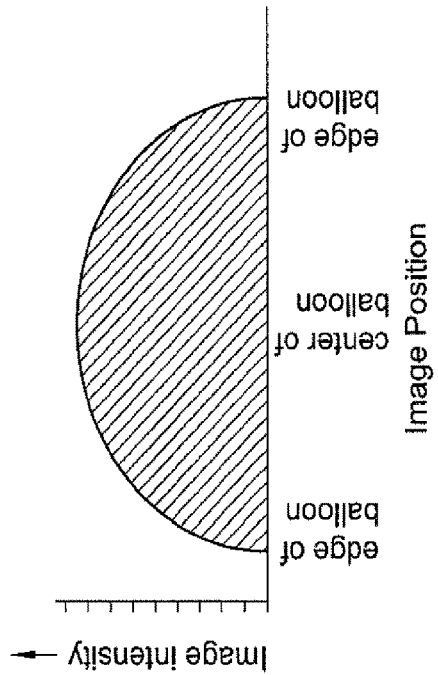
Figure 8:
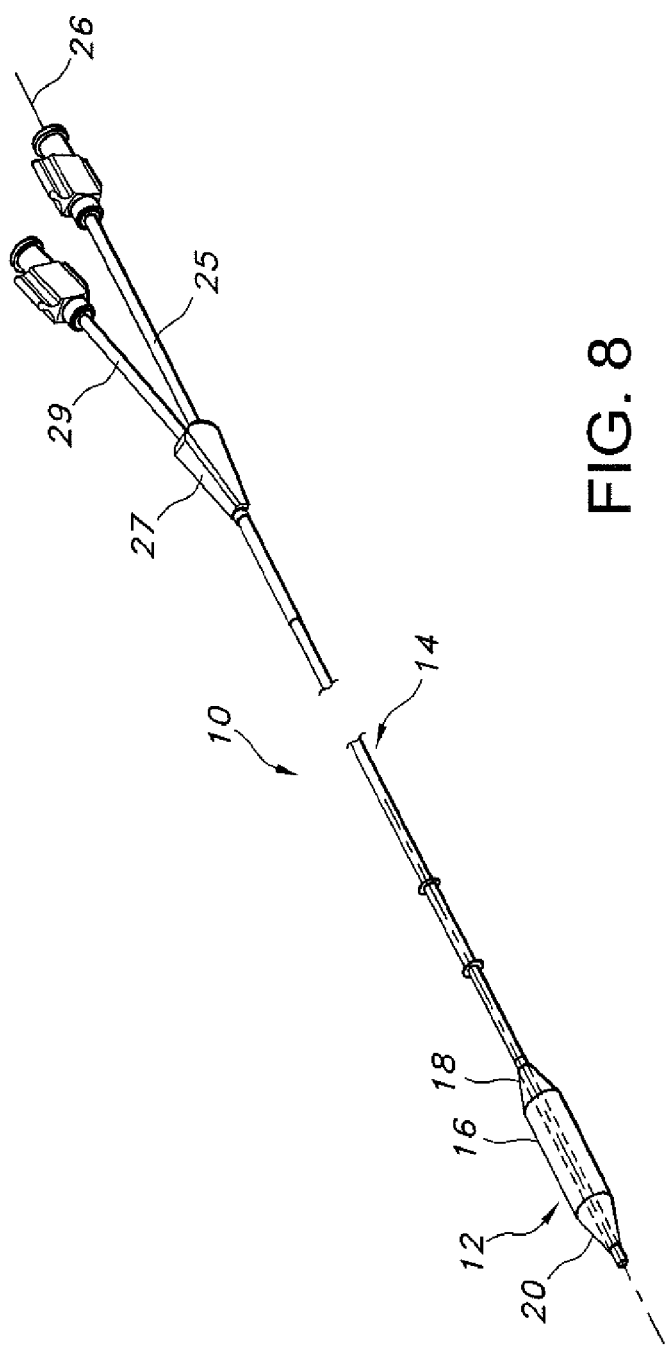

Provided is a catheter 10 having a distal portion 11 with a balloon 12 mounted on a catheter tube 14. Referring to FIGS. 6, 7, and 8, the balloon 12 when inflated has an intermediate section 16, or "barrel," and end sections 18, 20. In one embodiment, the end sections 18, 20 reduce in diameter to join the intermediate section 16 to the catheter tube 14 (and thus sections 18, 20 are generally termed cones or cone sections). The balloon 12 is sealed at balloon ends (proximal end 15*a* and distal end 15*b*) on the cone sections 18, 20 to allow the inflation of the balloon 12 via one or more inflation lumens 17 extending within catheter tube 14 and communicating with the interior of the balloon 12.

As noted above and can be understood with reference to FIGS. 5 and 6, the catheter tube 14 also includes a shaft S for supporting the balloon 12. The shaft S may be an elongated, tubular shaft 24 forming a guidewire lumen 23 that directs the guidewire 26 through the catheter 10, and along the distal end of which the balloon 12 may be located. The cone section 20 at the distal end 15*b* of the balloon 12 may be fixed to this shaft 24 adjacent the tip P. The balloon 12 at the opposite end is connected to the tube 14, and is able to move relative to shaft 24 in order to permit a degree of expansion in the longitudinal direction.

Figure 9:
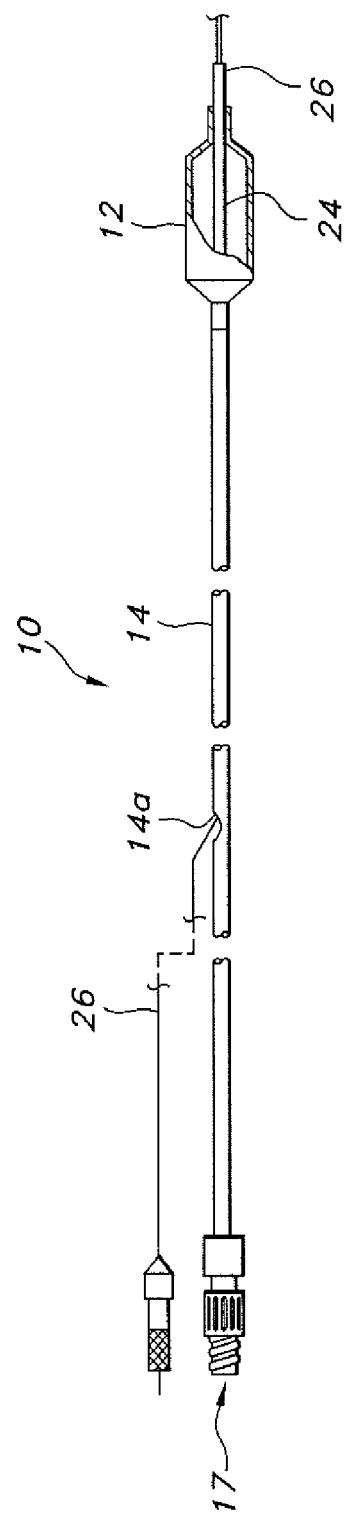

As illustrated in FIG. 8, this guidewire 26 may extend through the proximal end of the catheter 10 and a first port 25 of a connector 27 into the lumen 23 to achieve an "over the wire" (OTW) arrangement, but could also be provided in a "rapid exchange" (RX) configuration, in which the guidewire 26 exits a lateral opening 14*a* closer to the distal end (see FIG. 9) or else is fed through a passage associated with the tip P distally of the balloon 12 ("short" RX; not shown). A second port 29 may also be associated with catheter 10, such as by way of connector 27, for introducing a fluid (e.g., saline, a contrast agent, or both) into the interior compartment of the balloon 12 via the inflation lumen 17.

Balloon 12 may include a single or multi-layered balloon wall 28 forming the interior for receiving the inflation fluid. The balloon 12 may be a non-compliant balloon having a balloon wall 28 that maintains its size and shape in one or more directions when the balloon is inflated. Examples of non-compliant balloons may be found in U.S. Pat. No. 6,746,425 and U.S. Patent Application Publication Nos. 2006/0085022, 2006/0085023 and 2006/0085024, the disclosures of which are incorporated by reference. The balloon 12 may comprise PET and/or fiber reinforcements. The balloon 12 in such case also has a pre-determined surface area that remains substantially constant during and after inflation, also has a pre-determined length and pre-determined diameter that each, or together, remain substantially constant during and after inflation (subject to a relatively small amount of longitudinal expansion (e.g., up to 5%) as the result of the material properties). However, the balloon 12 could be semi-compliant or compliant instead, depending on the particular use. Examples of materials for compliant balloons include latex and silicone, and for semi-compliant balloons include polyamides (Nylon 11 or Nylon 12), polyimide block co-polymers (Pebax), polyurethanes (Pellethane), polycarbonate-based thermoplastic polyurethanes (Carbothane).

In order to provide for enhanced locatability during an interventional procedure, and potentially without the use of contrast media, the catheter 10 may have a radiopaque quality. In one embodiment, this radiopaque quality is provided in a manner that allows for a clinician to ensure the accurate positioning of the balloon 12 and, in particular, the working surface W created on inflation of the balloon, at a specified treatment area T. This may be especially important in the delivery of a particular treatment, such as a drug or stent, via the balloon working surface W, as outlined in more detail in the following description.

In one embodiment, the radiopaque quality may be achieved by one or more at least partially radiopaque markings or markers M associated with the catheter 10. In a first embodiment, as shown in FIG. 10, the arrangement includes at least one radiopaque marking or marker M. This marking or marker M may take the form of a radiopaque material, such as a band 30. The band 30 may be associated with the shaft 24 passing through the interior of the balloon 12 (which is schematically illustrated in FIG. 10 in the uninflated, wrapped or folded condition to facilitate travel within the vasculature).

The marking, such as band 30, may be positioned at an initial location O. This initial location O may be offset from the midpoint location A of the balloon 12 in the uninflated or wrapped condition. As illustrated, the midpoint location A is located between and spaced from the proximal and distal ends 15*a*, 15*b* of the balloon 12, along portion of the balloon wall 28 when folded that forms the barrel section 16 when the balloon 12 is inflated.

As indicated in FIG. 11, the offset location O of the marking or band 30 corresponds to the midpoint location B of the working surface W when inflated, such as may be the result of longitudinal expansion of the balloon 12 in the proximal direction C. Accordingly, the clinician may position the uninflated balloon 12 such that the marking or band 30 is at the desired midpoint or center region R of the treatment area T (such as a lesion), yet offset from the midpoint location A of the wrapped balloon 12, as indicated in FIG. 12. Given that the offset location O takes into account the amount of longitudinal expansion caused by inflation, the clinician is thus assured that the balloon 12, when inflated and expanded, creates the desired profile such that the working surface W corresponds to the treatment area T.

As should be appreciated, the marking or band 30 remains at or adjacent the center region R of the treatment area T, as originally placed in the uninflated condition, despite the expansion of the balloon 12 to form the working surface W and provide the desired treatment. Consequently, the incidence of a possible geographic "miss" is reduced. This is primarily because the balloon 12 expands in the longitudinal direction relative to its pre-positioning at the center region R of the treatment area T as a result of the offset marking, instead of being positioned using marker bands that do not necessarily correspond to the extent of the working surface W of the inflated balloon (see, e.g., FIG. 5).

The offset location O may be selected based on the predicted expansion of the balloon 12 in the longitudinal direction during inflation. For instance, the offset location O may be offset from the midpoint location A approximately 1-15% of the full length of the expanded or inflated balloon 12 (that is, the distance between the distal and proximal ends 15*a*, 15*b*). This includes the amounts of less than to about 1%, about 2%, about 3%, about 4%, about 5%, about 6%, about 7%, about 8%, about 9%, about 10%, about 11%, about 12%, about 13%, about 14%, and about 15%. The actual amount of offset used may be empirically determined or estimated, such as based on the properties of the materials used (including, for example, the type of material, shape, size, wall thickness, thermal expansion characteristics, and the like).

As indicated in FIG. 10, the offset location O may account for expansion in the proximal direction C upon inflation of the balloon 12. However, it is also possible to account for expansion in the distal direction D by positioning the marking, such as band 30, at a location distally from the midpoint location A, as shown in FIG. 14. Thus, as indicated in FIG. 15, the longitudinal expansion of the balloon 12 causes the marking or band 30 to align substantially with the midpoint location 13 of the working surface W in the desired manner. The positioning of the marker at the offset location O may also be such that it takes into account expansion in both the proximal and distal directions, C, D.

Figure 16:
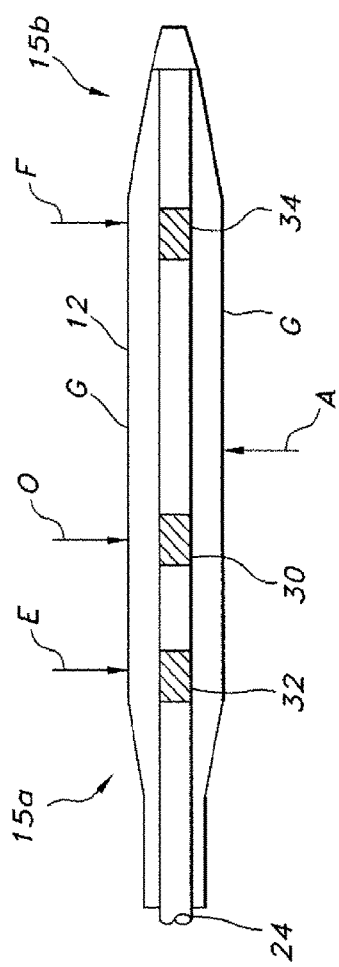
FIGS. 16 and 17 are additional views of yet another embodiment of a balloon catheter according to the disclosure.
Figure 17:
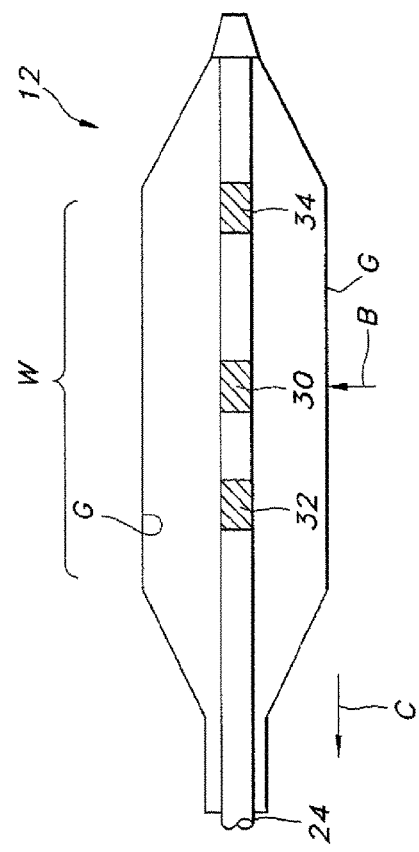

Turning to FIGS. 16 and 17, it can be understood that further markings or markers may be provided on the catheter 10, such as within the balloon 12. For example, markings or markers may be associated with the shaft 24 in the form of bands 32, 34. These bands 32 may be formed at least partially of a radiopaque material. The bands 30, 32 initially indicate locations E, F adjacent the proximal and distal ends 15a, 15b of the balloon 12 in the uninflated condition, and thus aid the clinician in understanding the relative location of the distal and proximal ends 15a, 15b of the balloon 12. The marking, such as band 30, at the offset location O is thus used to position the balloon 12 in connection with the other markings or markers (e.g., bands 32, 34) prior to inflation, but the expansion is such that the midpoint location B of the working surface W corresponds to the location of the band 30 on inflation.

Thus, as can be appreciated, at least three markings or markers are present in this embodiment, such as bands 30, 32, 34, and which markings or markers are not spaced equidistantly in the longitudinal direction. For example, in the illustrated embodiment, band 30 is closer to proximal band 32 than distal band 34. In other words, the non-radiopaque portion separating one pair of markings or markers is larger or smaller than the non-radiopaque material separating the other pair of markings or markers. Despite this irregular spacing, all three markings or markers in the illustrated embodiment remain within the interior compartment of the balloon 12 and, in particular, the portion corresponding to the working surface W.

Markings or markers may also be provided on the balloon 12 in order to help determine relative locations during the procedure. For example, as shown in FIGS. 18 and 19, the marking offset from the midpoint location A may be provided in the form of a band 30 along the shaft 24, and a marking 36 may be associated with the balloon 12, such as along the conical portion or section 20 adjacent the tip P at the distal end of the catheter 10 (but possibly at the proximal end instead, or at both locations). Thus, as a result of the longitudinal expansion of the balloon 12 on inflation, the marking or band 30 on the shaft 24 aligns with the midpoint location B of the working surface W. The marking on the balloon 12 may comprise a foil, film, adhesive, coating, or the like applied on the surface or within one or more interior layers forming the balloon wall 28. Also, such a marking may also be provided on conical portion 18 of balloon 12 for indicating the proximal end of the working surface W.

With reference to FIG. 20, the catheter 10 may be provided with one or more markings or markers M for use in measuring a dimension within a vessel. The markings or markers M may be radiopaque in nature, and may be applied to a tubular member within the catheter 10, such as the guidewire tubular member 24. The markings or markers M may by applied within the balloon 12 so as to measure a dimension of a structure, such as a lesion to be dilated, within a vessel, as may be seen, for example, in FIGS. 27 and 28. In one aspect, the markings or markers M may act as a ruler to measure a linear distance when positioned within the vessel.

FIGS. 21-25 illustrate certain embodiments of the catheter 10 with markings or markers M placed at various distances from one another and upon various elements of the catheter 10. As shown in FIG. 21, the markings or markers M may be equidistant from one another. These markings or markers M may be placed along the guidewire tubular member 24 within the balloon 12 alone as shown in FIG. 20, or along the guidewire tubular member 24 both within the balloon 12 and along the catheter 10 outside of the balloon 12, as shown in FIG. 21. As should be appreciated, at least three markings or markers M appear in the interior of balloon 12 in the illustrated embodiment and, in particular, within the boundary of the location providing the balloon working surface W (that is, one marking or marker is provided adjacent to a first edge of the working surface W, a second marker or marking is provided adjacent to a second edge of the working surface W, and a third marking or marker is between the two edge markings or markers).

In certain embodiments, as shown in FIGS. 20 and 21, the markings or markers M may be placed equidistant from one another along the entire length of the catheter 10, including the portion including the balloon 12. The distance between the markings or markers M may range from small distances for measuring fine measurements (e.g., less than about 1 millimeter between markings or markers M and up to about 10 millimeters), average or medium measurements (e.g., about 10 millimeters between markings or markers M), or large measurements (e.g., greater than 10 millimeters between markings or markers M).

Figure 22:
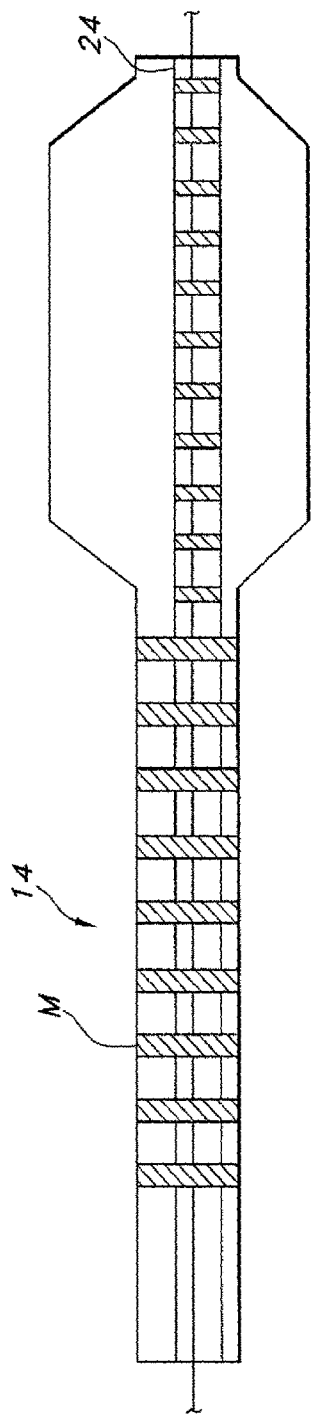
FIGS. 22 and 23 are partially cutaway, schematic side views showing various markings or markers on a balloon catheter according to one embodiment of the disclosure.

FIG. 22 illustrates a further embodiment of the catheter 10 including markings or markers M. In this embodiment, the markings or markers M may be positioned on the catheter tube 14. In one aspect, the markings or markers M may be placed on the catheter tube 14, such as along the outer surface. The markings or markers M may be on the catheter tube 14 alone, or as illustrated, the markings or markers may be on both the catheter tube 14 and the guidewire tubular member 24. The markings or markers M may be equidistant from each other, or may be non-equidistant.

Figure 23:
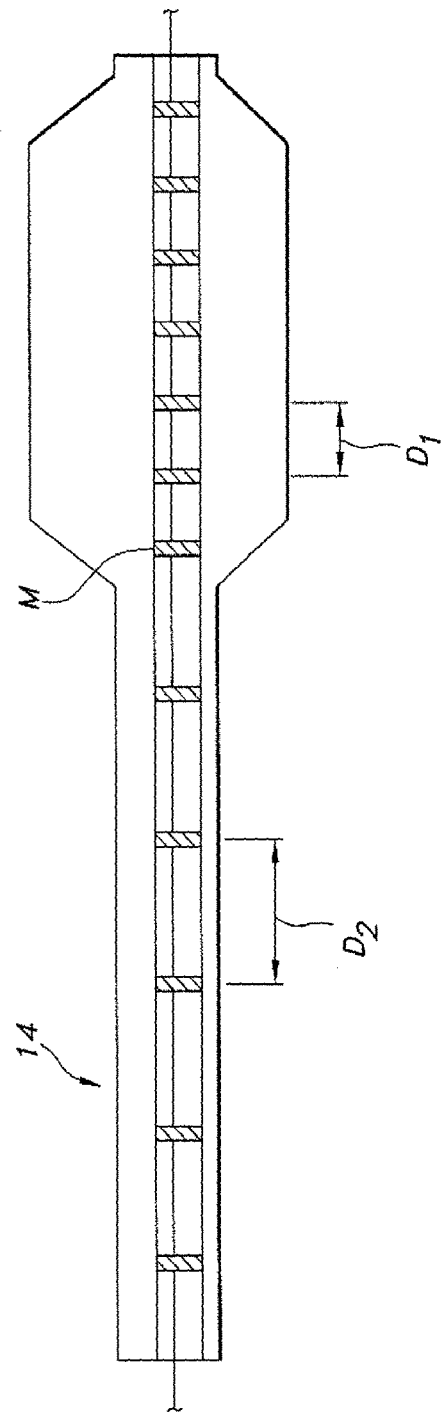

With reference to FIG. 23, the markings or markers M may be positioned with a first distance $D_1$ between markings or markers M at a first location on the catheter, and with a second distance $D_2$ between markings or markers M at a second location on the catheter. In one example, the markings or markers M within the balloon 12 may be positioned with a first distance $D_1$ between the markings or markers, while the markings or markers M at a position outside the balloon along the catheter tube 14 may be positioned with a second distance $D_2$ between markings or markers. In the illustrated embodiment, the first distance $D_1$ may be less than the second distance $D_2$. This may allow for gross measurements of distance on a proximal portion of the catheter 10, while allowing for more fine measurements of a distance on a distal portion of the catheter 10.

Figure 24:
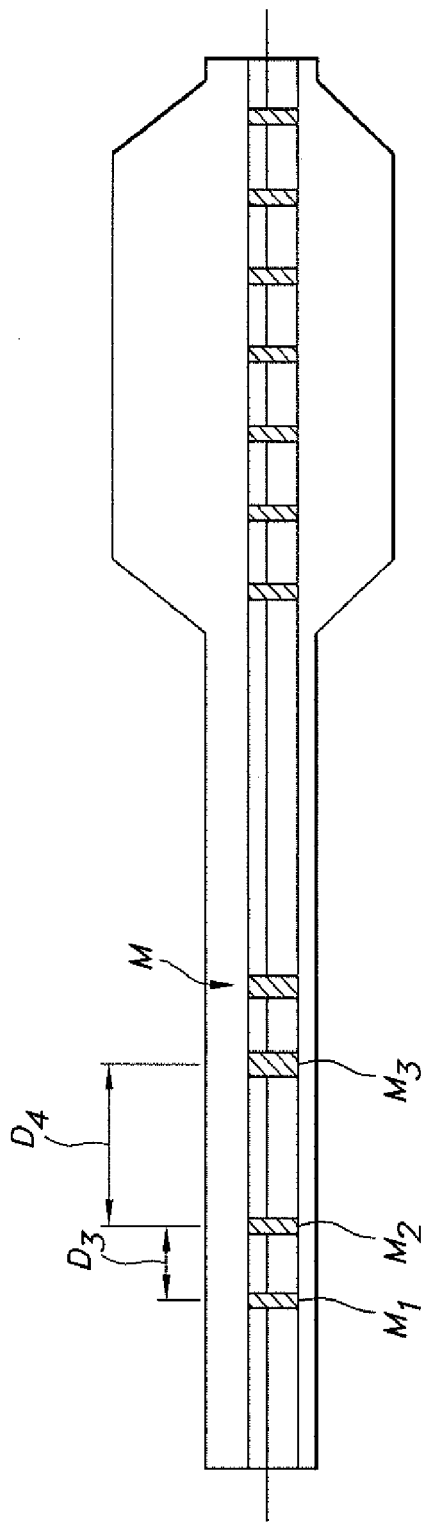
FIGS. 24 and 25 are partially cutaway, schematic side views showing markings or markers on a balloon catheter according to one embodiment of the disclosure.

FIG. 24 illustrates a further embodiment in which markings or markers M may be positioned with varying distances therebetween, such that the markings or markers M are not equidistant from one another. As shown, a third distance $D_3$ may exist between first and second adjacent markings or markers $M_1$, $M_2$. Additionally, second and third adjacent markings or markers $M_2$, $M_3$ may be positioned such that a fourth distance $D_4$ separates these markings or markers $M_2$, $M_3$. The third distance $D_3$ may be less than the fourth distance $D_4$. In one embodiment, the third distance $D_3$ may be, for example, about 5 millimeters, and the fourth distance $D_4$ may be, for example, about 10 millimeters. The distance between markings or markers M may alternate between the third distance $D_3$ and the fourth distance $D_4$ along the length of the catheter 10. This alternating distance between markings or markers M may allow for fine or gross measurements at various points along the length of the catheter 10.

Figure 25:
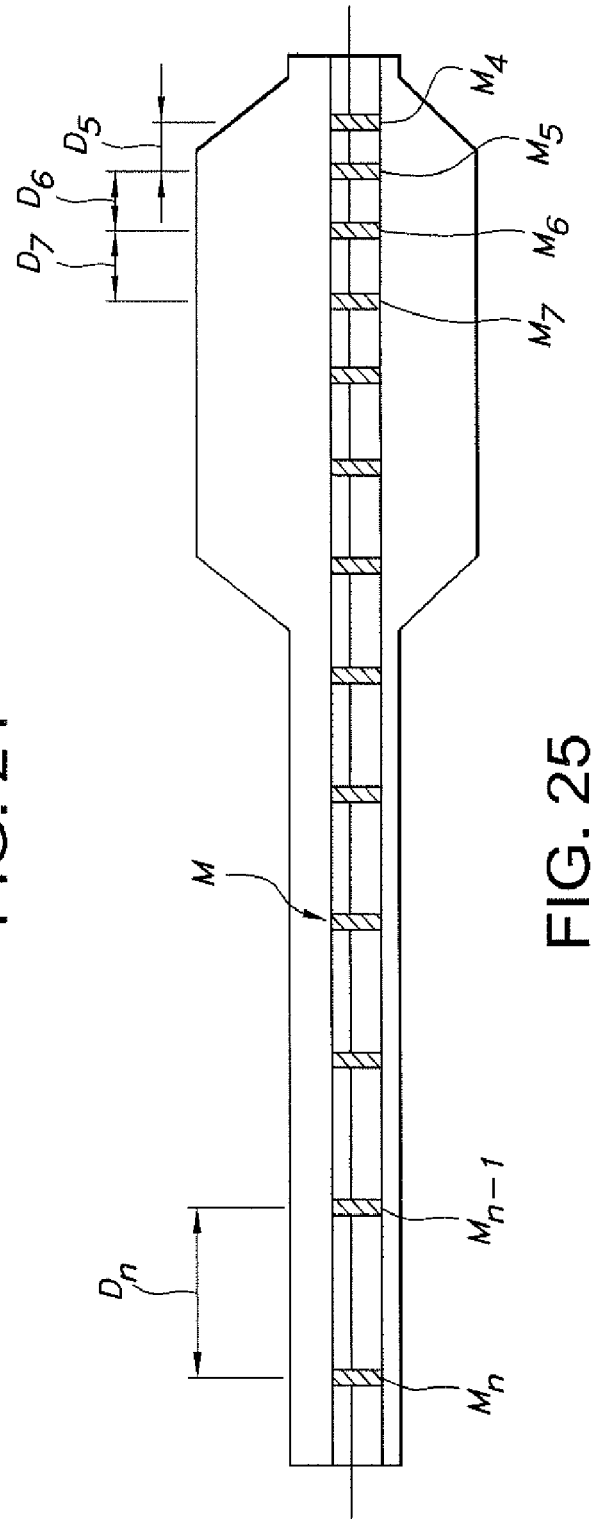

With reference to FIG. 25, another embodiment is disclosed wherein the markings or markers $M_4$, $M_5$, $M_6$ ... $M_n$ may be placed along the catheter 10 in a non-equidistant manner. As shown, the distance between markings or markers M may increase from a distal end of the catheter 10 to a proximal end of the catheter 10. For example, a fifth distance $D_5$ may exist between fourth and fifth markings or markers $M_4$, $M_5$ on a distal end of the catheter 10. Similarly, a sixth distance $D_6$, proximal to the fifth distance $D_5$, may exist between the fifth and sixth markings or markers $M_5$, $M_6$, and a seventh distance $D_7$ may exist between the sixth and seventh markings or markers $M_6$, $M_7$. The distance between each successive pair of adjacent markings or markers M from a distal end of the catheter 10 to a proximal end of the catheter 10 may incrementally increase with respect to the previous pair of markings or markers M through a final distance $D_n$. In the FIG. 25 example, $D_5 < D_6 < D_7 < \ldots D_n$. Stated another way, the distance between markings or markers M may incrementally and continually decrease from a proximal end of the catheter 10 to a distal end. This decrease in distance between adjacent markings or markers M may allow for progressively finer measurements to be taken toward the distal end of the catheter 10.

Figure 26:
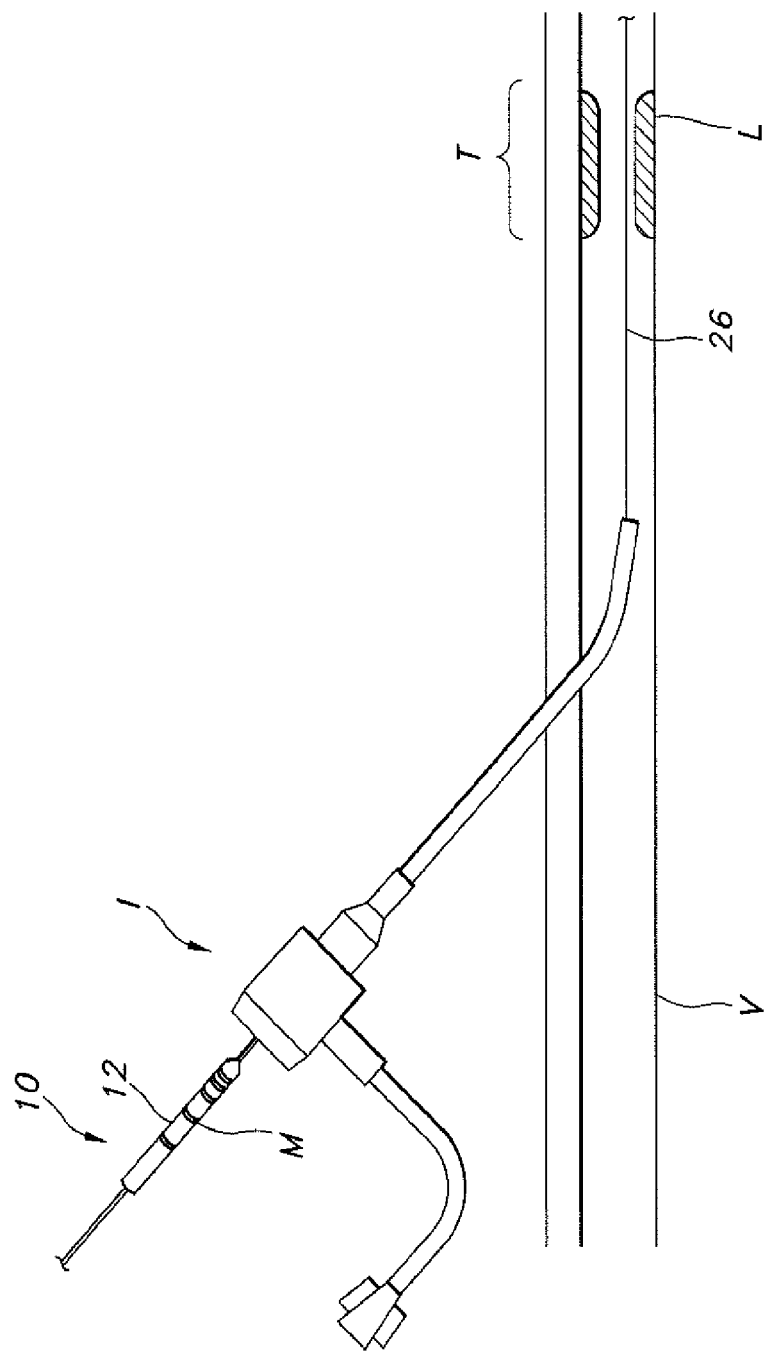
FIGS. 26, 27, and 28 illustrate an exemplary use of a balloon catheter according to the disclosure.
Figure 27:
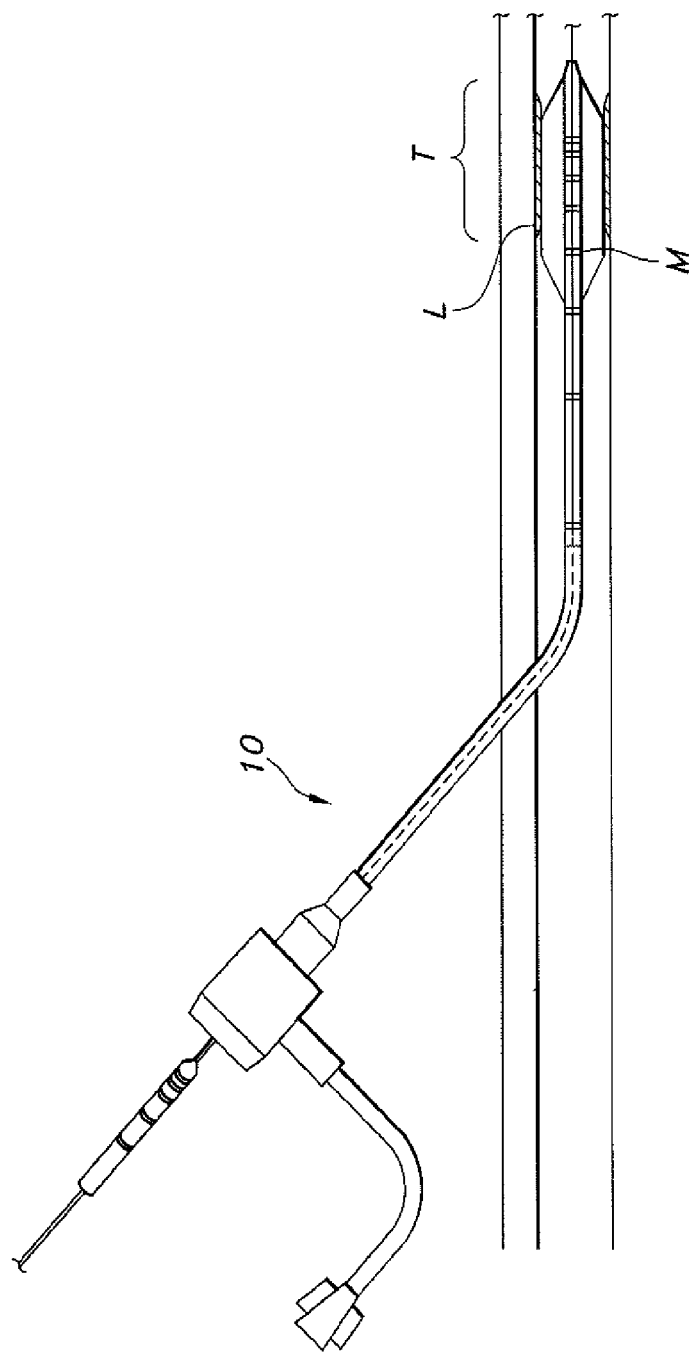
Figure 28:
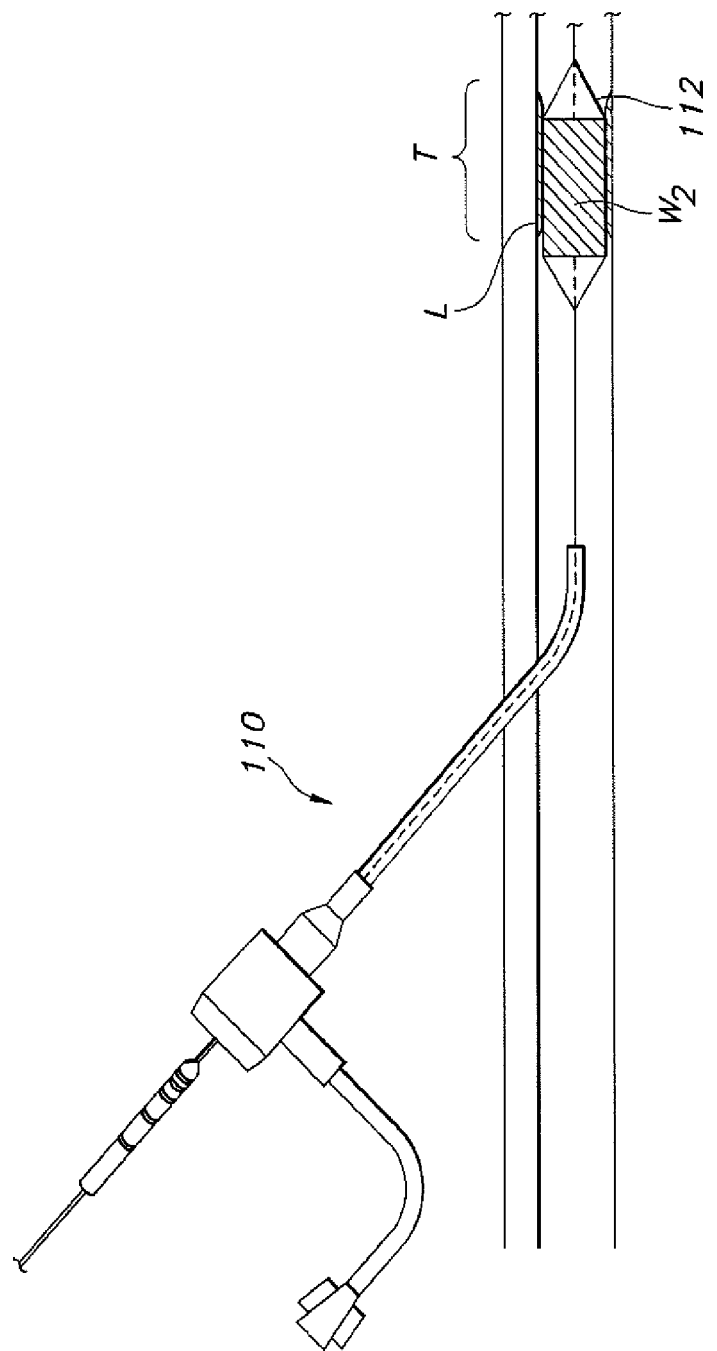

FIGS. 26-28 illustrate uses of a catheter 10 with radiopaque markings or markers M for measuring a treatment area T and delivery of a treatment balloon 112 to the treatment area T. FIG. 26 shows a balloon 12 of the catheter 10 including a plurality of markings or markers M being inserted along a guidewire 26 into a vessel V to a treatment area T, such as a lesion L, using a device called an introducer I. The balloon 12 may be inflated at the treatment area T so as to dilate the vessel V and compress the lesion L, as shown in FIG. 27. The balloon 12 may be deflated and removed after use.

The plurality of markings or markers M along the catheter 10 may be spaced at pre-determined intervals from one another so as to demarcate known distances therebetween. These markings or markers M may be used to measure a length of the treatment area T, which in the illustrated embodiment constitutes the distance spanning the length of lesion L. Markings or markers M may be used to measure the length of the treatment area T before and/or after dilation of the balloon 12. With precise measurement of the desired or necessary treatment area T, the user may select an appropriate treatment balloon 112 for the task (which may also be provided as part of a combination with a measuring balloon). For example, the user may select a treatment balloon 112 with a working surface corresponding in length to the measurement obtained, or an associated treatment catheter 110 (FIG. 28) for treatment with markers or markings corresponding to the markers or markings of the catheter 10

As shown in FIG. 28, the selected treatment catheter 110 (which again may be substantially identical in construction to catheter 10, and may thus include matching radiopaque markings or markers, including for example an offset marking for aligning with the center region) may then be inserted to position the treatment balloon 112 at the treatment area T. The treatment balloon 112 may include a working surface $W_2$ including a treatment, such as for example a therapeutic agent (e.g., a drug, such as paclitaxel, rapamycin, heparin and the like), a stent, a stent graft, or a combination). In some cases, the treatment balloon 112 may be longer than the balloon of the measuring catheter (so as to ensure full coverage of the lesion L during the subsequent intervention; e.g., the first balloon may be 20 millimeters, and the second balloon may be 40 millimeters). Common positioning of the catheters 10, 110 may be done in relation to a common location within the body visible under fluoroscopy, such as a bony landmark (e.g., a particular vertebrae).

In the case of delivering a treatment, selection of a length of working surface $W_2$ may be important so as to treat the entire treatment area T, but to treat no more than treatment area T. A treatment balloon 112 with a length of a working surface $W_2$ corresponding to the measured distance of the treatment area T may be selected based on the measured length of treatment area T with the measuring catheter 10. In this manner, a clinician may be assured that the delivery of the treatment is achieved in the intended manner to the entire treatment area T, but not elsewhere, which may aid in avoiding geographic misalignment, failure to treat an entire treatment area T, or overdose of the therapeutic agent outside the treatment area T. Consequently, the procedure is potentially shortened, and a further intervention may be avoided. The measurement technique may also be used post-dilatation, if desired.

As suggested by the foregoing, any of the disclosed balloons 12 may carry treatment in the form of one or more treatment agents, such as a payload (drug, stent, or both) or a working implement (cutter, focused force wire, or the like). For example, as shown in FIG. 17, a balloon 12 with a defined working surface W (such as by providing markings or markers M in the form of radiopaque bands 32, 34 at the transitions between the barrel section 16 and end sections 18, 20), may include at least a portion coated with such a drug G, such as one designed for achieving a desired therapeutic effect when applied to the interior of the vessel. The drug G forming this treatment may be applied to the balloon 12 as part of the manufacturing process, including possibly prior to folding for insertion in the vasculature or after folding is completed. The clinician may thus with the benefit of a fluoroscope determine the precise positioning of the working surface W prior to inflating the balloon 12 in the vasculature to deliver the drug G to the desired location and provide the desired treatment, which may form part of a treatment regimen.

Examples of radiopaque materials that may be used herein for the markings or markers on the catheter 10 (balloon 10 or shaft 24) include, but are not limited to, finely divided tungsten, tantalum, bismuth, bismuth trioxide, bismuth oxychloride, bismuth subcarbonate, other bismuth compounds, barium sulfate, tin, silver, silver compounds, rare earth oxides, and many other substances commonly used for X-ray absorption. The amount used may vary depending on the desired degree of radiopacity, and in any form (e.g., bands, foil, films (including with embedded radiopaque powders), decals, paints, coatings, etc.). In one embodiment, the markings or markers M may comprise a polymer loaded with a radiopaque element such as iodine, iopromide, metallic ions, gold, barium sulfate, tungsten, bismuth trioxide, or other similarly functional materials. The radiopaque materials may be used in the form of gels, powders, dust, particles, nano-particles, liquids, stains, adhesives and the like. The radiopaque material forming the marking or marker could be anywhere from about 5-95% radiopaque or, more specifically, in the range of about 70-90% radiopacity.

The markings or markers M may take the form of metal marker bands, such as platinum, iridium and/or gold markings or markers, which may be swaged, glued, or otherwise affixed to the catheter 10. In one embodiment, the catheter may include heat-bonded radiopaque segments interspersed between non-radiopaque segments. In a further embodiment, the markings or markers M may comprise a radiopaque tape or film applied to the catheter 10. A radiopaque ink may also be used to form the markings or markers M. While bands are mentioned above and illustrated in the figures, the markings or markers M may take the form of symbols (numbers, letters), geometric shapes (gradation lines, hash marks, dots, etc.), or combinations of one or more of the foregoing. The aforementioned marking or marker compounds are exemplary of various radiopaque markings or markers currently used in medicine, but the marking or marker may include any technique that allows for visualization of a particular location during use in the vasculature.

While the disclosure presents certain embodiments to illustrate the inventive concepts, numerous modifications, alterations, and changes to the described embodiments are possible without departing from the sphere and scope of the present invention, as defined in the appended claims. For example, any ranges and numerical values provided in the various embodiments are subject to variation due to tolerances, due to variations in environmental factors and material quality, and due to modifications of the structure and shape of the balloon, and thus can be considered to be approximate and the term "approximately" means that the relevant value can, at minimum, vary because of such factors. Also, the drawings, while illustrating the inventive concepts, are not to scale, and should not be limited to any particular sizes or dimensions. Accordingly, it is intended that the present disclose not be limited to the described embodiments, but that it has the full scope defined by the language of the following claims, and equivalents thereof.

The invention claimed is:

1. A balloon catheter for insertion in a vessel for treating a treatment area, comprising:
    a shaft;
    an inflatable balloon having a distal end fixed to the shaft and having an interior; and
    at least three radiopaque markings spaced along a longitudinal axis of the catheter on the shaft in the interior of the balloon, wherein a first distance separating a first radiopaque marking from a second adjacent radiopaque marking is different from a second distance separating the second radiopaque marking from a third adjacent radiopaque marking;
    wherein the balloon includes a midpoint, wherein the midpoint is located at a first longitudinal location in an uninflated condition and at a second longitudinal location in an inflated condition;
    wherein the second radiopaque marking is positioned at an offset location relative to the first longitudinal location, and wherein the second radiopaque marking is positioned at a fixed longitudinal location relative to the distal end,
    whereby on inflation of the balloon, the midpoint substantially aligns with the second radiopaque marking.

2. The balloon catheter of claim 1, wherein the catheter shaft further includes an inner tubular member forming a guidewire lumen, and wherein the inner tubular member comprises the at least three radiopaque markings.

3. The balloon catheter of claim 1, wherein the shaft includes an outer wall having at least one of the first or second radiopaque markings.

4. The balloon catheter of claim 1, wherein the first distance is smaller than the second distance and the first radiopaque marking is proximal to the second radiopaque marking, which is proximal to the third radiopaque marking along the longitudinal axis.

5. The balloon catheter of claim 1, wherein the at least three radiopaque markings are arranged in a pattern comprising a plurality of adjacent pairs, and wherein the adjacent pairs are alternatingly separated by the first and second distances.

6. The balloon catheter of claim 1, wherein the radiopaque markings are arranged in a pattern comprising adjacent radiopaque markings spaced at progressively larger distances from one another from a distal point on the catheter to a proximal point on the catheter.

7. The balloon catheter of claim 1, wherein the balloon includes a working surface, and wherein the first radiopaque marking corresponds to at least one end of the working surface of the balloon.

8. The balloon catheter of claim 7, wherein the third radiopaque marking on the shaft is provided at a location corresponding to another end of the working surface.

9. The balloon catheter of claim 1, wherein the offset location is spaced from the first longitudinal location in a proximal direction.

10. The balloon catheter of claim 1, wherein the offset location is spaced from the first longitudinal location in a distal direction.

11. The balloon catheter of claim 1, wherein the offset location is spaced from the first longitudinal location a distance approximately 1-15% of a length between a distal end and a proximal end of the balloon in the inflated condition.

12. The balloon catheter of claim 1, further including at least one radiopaque marking external to the interior of the balloon.

13. The balloon catheter of claim 12, wherein the external radiopaque marking is located on the shaft.

14. The balloon catheter of claim 12, further including an outer, tubular shaft forming an inflation lumen for supplying an inflation fluid to the balloon, and wherein the external radiopaque marking is located on the outer tubular shaft.

15. The balloon catheter of claim 1, further including a plurality of radiopaque markings external to the interior of the balloon, wherein the external markings are equidistantly spaced.

16. The balloon catheter of claim 1, further including a plurality of radiopaque markings external to the interior of the balloon, wherein the external markings are irregularly spaced.

17. The balloon catheter of claim 1, wherein the markings comprise bands formed at least partially of a radiopaque material.

18. The balloon catheter of claim 1, wherein in the uninflated condition the first radiopaque marking aligns with a first end of a working surface of the balloon in the uninflated condition and the third radiopaque marking aligns with a second end of the working surface of the balloon in the uninflated condition.

19. A balloon catheter for insertion in a vessel for treating a treatment area, comprising:
    a shaft;
    an inflatable balloon having a distal end fixed to the shaft, said inflatable balloon having an interior;
    at least three radiopaque markings extending along a longitudinal axis of the catheter on the shaft and located within the interior of the balloon, wherein a first amount of non-radiopaque material separating a first radiopaque marking from a second radiopaque marking is different from a second amount of non-radiopaque material separating the second radiopaque marking from a third radiopaque marking;

wherein:
- the balloon includes a midpoint, wherein the midpoint is located at a first longitudinal location in an uninflated condition and at a second longitudinal location in an inflated condition; and
- the second radiopaque marking is positioned at an offset location relative to the first longitudinal location, and wherein the second radiopaque marking is positioned at a fixed longitudinal location relative to the distal end;

whereby on inflation of the balloon, the midpoint substantially aligns with the at least one radiopaque marking.

20. The balloon catheter of claim 19, wherein in the uninflated condition the first radiopaque marking aligns with a first end of a working surface of the balloon in the uninflated condition and the third radiopaque marking aligns with a second end of the working surface of the balloon in the uninflated condition.

\* \* \* \* \*